(12) United States Patent
Elghazzawi et al.

(10) Patent No.: US 10,617,600 B2
(45) Date of Patent: *Apr. 14, 2020

(54) SYSTEM FOR ASSISTING RESCUERS IN PERFORMING CARDIO-PULMONARY RESUSCITATION (CPR) ON A PATIENT

(71) Applicant: ZOLL Medical Corporation, Chelmsford, MA (US)

(72) Inventors: Ziad F. Elghazzawi, Newton, MA (US); Jing Pan, Newton, MA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 530 days.

This patent is subject to a terminal disclaimer.

(21) Appl. No.: 15/601,465

(22) Filed: May 22, 2017

(65) Prior Publication Data
US 2017/0354569 A1 Dec. 14, 2017

Related U.S. Application Data

(63) Continuation of application No. 15/178,578, filed on Jun. 10, 2016, now Pat. No. 9,682,009, which is a
(Continued)

(51) Int. Cl.
| | |
|---|---|
| A61N 1/00 | (2006.01) |
| A61H 31/00 | (2006.01) |
| A61B 5/11 | (2006.01) |
| A61N 1/362 | (2006.01) |
| A61N 1/39 | (2006.01) |

(Continued)

(52) U.S. Cl.
CPC ......... A61H 31/005 (2013.01); A61B 5/0059 (2013.01); A61B 5/02 (2013.01); A61B 5/0205 (2013.01); A61B 5/0402 (2013.01); A61B 5/113 (2013.01); A61B 5/1114 (2013.01); A61B 5/7207 (2013.01); A61B 5/742 (2013.01);
(Continued)

(58) Field of Classification Search
CPC .. A61N 1/36014; A61N 1/3603; A61N 1/362; A61N 1/3625; A61N 1/3629; A61N 1/37; A61N 1/37258; A61N 1/3904; A61N 1/39046; A61N 1/39044; A61H 31/00; A61H 31/004; A61H 31/005
See application file for complete search history.

(56) References Cited

U.S. PATENT DOCUMENTS

| | | | |
|---|---|---|---|
| 5,683,424 A | 11/1997 | Brown et al. | |
| 7,220,235 B2 | 5/2007 | Geheb et al. | |

(Continued)

Primary Examiner — Allen Porter
(74) Attorney, Agent, or Firm — The Webb Law Firm

(57) ABSTRACT

A system for assisting a rescuer includes: a chest compression sensor configured to sense movement of the patient's chest and a second sensor configured to sense information indicative of whether the rescuer's hand is in contact with or is not in contact with the patient's chest. The second sensor is configured to be positioned on the patient's chest at a location corresponding to a location of the rescuer's hand when delivering chest compressions to the patient's chest. The system also includes a feedback device and a computing unit. The computing unit is configured to cause the feedback device to provide chest compression feedback based on a determined chest compression rate and chest compression depth and to provide chest release feedback based on a determination of whether the rescuer is releasing the chest in between chest compressions.

20 Claims, 8 Drawing Sheets

Related U.S. Application Data continuation of application No. 14/605,653, filed on Jan. 26, 2015, now Pat. No. 9,387,147, which is a continuation of application No. 14/107,066, filed on Dec. 16, 2013, now Pat. No. 8,979,764, which is a continuation of application No. 13/555,439, filed on Jul. 23, 2012, now Pat. No. 8,634,937.

(60) Provisional application No. 61/527,663, filed on Aug. 26, 2011.

(51) Int. Cl.

| | | |
|---|---|---|
| *A61N 1/04* | (2006.01) | |
| *A61N 1/36* | (2006.01) | |
| *A61B 5/02* | (2006.01) | |
| *A61B 5/00* | (2006.01) | |
| *A61B 5/0205* | (2006.01) | |
| *A61B 5/113* | (2006.01) | |
| *A61B 5/0402* | (2006.01) | |

(52) U.S. Cl.
CPC .............. *A61N 1/39* (2013.01); *A61N 1/3925* (2013.01); *A61B 5/6823* (2013.01)

(56) References Cited

U.S. PATENT DOCUMENTS

| | | |
|---|---|---|
| 7,220,335 B2 | 5/2007 | Van Gompel et al. |
| 8,010,190 B2 | 8/2011 | Olson et al. |
| 8,034,006 B2 | 10/2011 | Celik-Butler et al. |
| 8,435,193 B2 | 5/2013 | Belalcazar |
| 8,615,295 B2 | 12/2013 | Savage et al. |
| 8,634,937 B2 | 1/2014 | Elghazzawi et al. |
| 8,738,129 B2 | 5/2014 | Packer et al. |
| 8,880,166 B2 | 11/2014 | Tan et al. |
| 8,979,764 B2 | 3/2015 | Elghazzawi et al. |
| 9,387,147 B2 | 7/2016 | Elghazzawi et al. |
| 2008/0312565 A1 | 12/2008 | Celik-Butler et al. |
| 2008/0312708 A1 | 12/2008 | Snyder |
| 2011/0040217 A1 | 2/2011 | Centen |
| 2011/0172572 A1 | 7/2011 | Belalcazar |
| 2011/0284004 A1 | 11/2011 | Silver et al. |

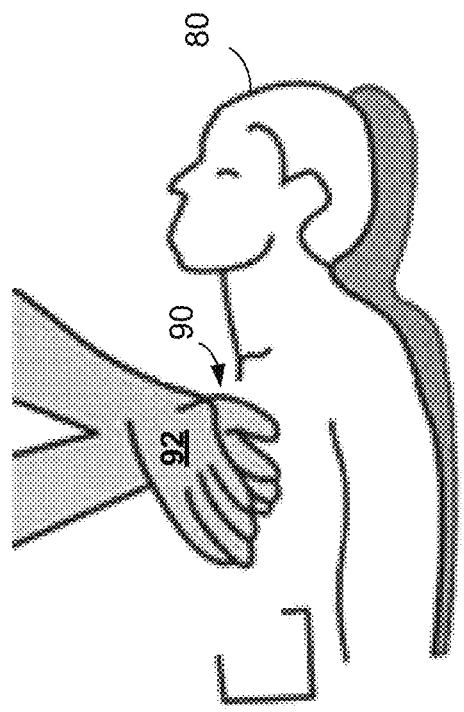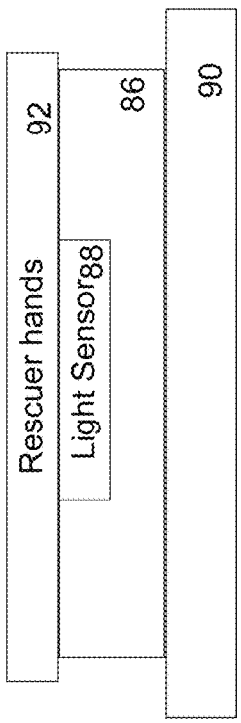
FIG. 6A FIG. 6B
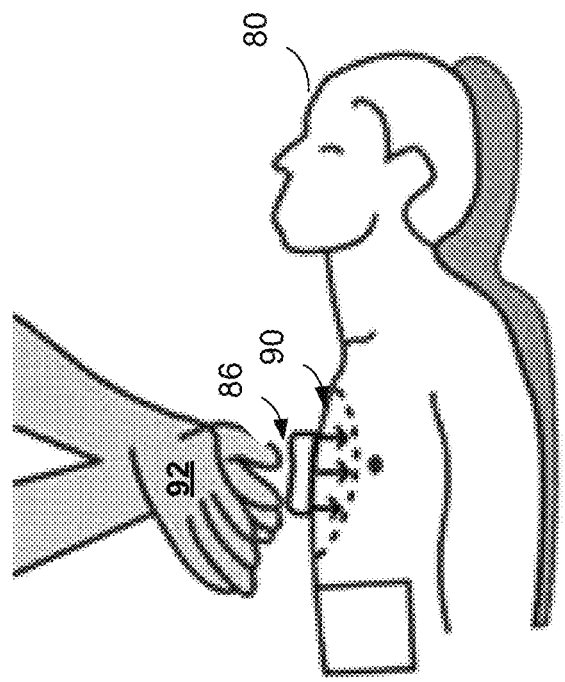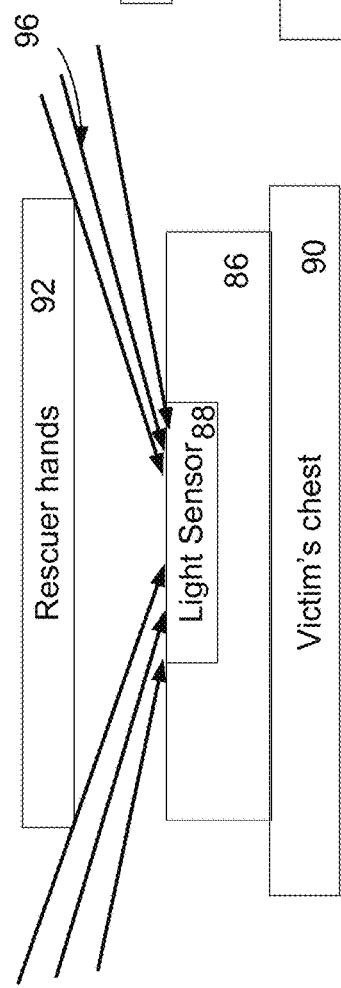
FIG. 7A FIG. 7B

SYSTEM FOR ASSISTING RESCUERS IN PERFORMING CARDIO-PULMONARY RESUSCITATION (CPR) ON A PATIENT

CROSS-REFERENCE TO RELATED APPLICATIONS

This application is a continuation of U.S. patent application Ser. No. 15/178,578, filed Jun. 10, 2016, which is a continuation of U.S. patent application Ser. No. 14/605,653, filed Jan. 26, 2015, now U.S. Pat. No. 9,387,147, which is a continuation of U.S. patent application Ser. No. 14/107,066, filed Dec. 16, 2013, now U.S. Pat. No. 8,979,764, which is a continuation of U.S. patent application Ser. No. 13/555,439 filed on Jul. 23, 2012, now U.S. Pat. No. 8,634,937, which claims priority to U.S. Provisional Application No. 61/527,663 filed Aug. 26, 2011, each of which is incorporated by reference herein in its entirety.

TECHNICAL FIELD

This document relates to cardiac resuscitation, and in particular to systems and techniques for assisting rescuers in performing cardio-pulmonary resuscitation (CPR).

BACKGROUND

The heart relies on an organized sequence of electrical impulses to beat effectively. Deviations from this normal sequence is known as arrhythmia. Certain medical devices include signal processing software that analyzes electrocardiography (ECG) signals acquired from a medical patient (e.g., a victim at a scene of an emergency) to determine when a cardiac arrhythmia such as ventricular fibrillation (VF) or shockable ventricular tachycardia (VT) exists. These devices include automated external defibrillators (AEDs), ECG rhythm classifiers, and ventricular arrhythmia detectors. An AED is a defibrillator—a device that delivers controlled electrical shock to a patient—while being relatively easy to use, such as by providing verbal prompts to a provider of care to "talk" the provider through a process of evaluating a patient for, attaching the patient to, and activating, AED therapy. Certain of the medical devices just discussed are also capable of recognizing different cardiac waveforms such normal sinus rhythm, aystole, VT and VF.

Many AEDs implement algorithms to recognize the VT and VF waveforms by performing ECG analyses at specific times during a rescue event of a patient using defibrillation and cardio-pulmonary resuscitation (CPR). The first ECG analysis is usually initiated within a few seconds after the defibrillation electrodes are attached to the patient. Typically, if the ECG analysis detects a shockable rhythm, the rescuer is advised to deliver a defibrillation shock.

Following the defibrillator shock delivery or when any of the analyses described above detects a non-shockable rhythm, treatment protocols recommended by the American Heart Association and European Resuscitation Council require performing CPR on the victim for a period of two minutes. The CPR includes rescue breathing and chest compressions. Following this period of CPR, the AED reinitiates ECG analysis as described above. The sequence of one ECG analysis/defibrillation shock followed by 2 minutes of CPR continues in a repetitive fashion for as long as the AED's power is turned on and the patient is connected to the AED device. Typically, the AED provides audio prompts to inform the rescuer when analyses are about to begin, what the analysis results were, and when to start and stop the delivery of CPR.

Many studies have reported that the discontinuation of precordial compression can significantly reduce the recovery rate of spontaneous circulation and 24-hour survival rate for victims. Thus, it is useful to recognize abnormal heart rhythms during chest compressions. There is recent clinical evidence showing that performing chest compressions before defibrillating the patient under some circumstances can be beneficial. Specifically, it is clinically beneficial to treat a patient with chest compressions before defibrillation if the response times of the medical emergency system result in a delay of more than four minutes, such that the patient is in cardiac arrest for more than four minutes. Chest compression artifact rejection can employ spectral analysis of the ECG, defibrillation success prediction, and therapeutic decision-making typically specify a set of parameters in the ECG frequency spectrum to be detected. For example, U.S. Pat. No. 5,683,424 compares a centroid or a median frequency or a peak power frequency from a calculated frequency spectrum of the ECG to thresholds to determine if a defibrillating shock is necessary.

SUMMARY

In some aspects, a method for providing adaptive Cardiopulmonary Resuscitation (CPR) treatment to a person in need of emergency assistance includes obtaining, by a computing unit, from an accelerometer positioned to move in coordination with a patient's breastbone values for depths of a plurality of the chest compressions. The method also includes obtaining, by a computing unit, from a light sensor affixed to the patient information about light detection. The method also includes determining, based on the information from the light sensor, whether a rescuer is releasing the chest of a patient during manual CPR chest compressions. The method also includes providing feedback to a rescuer about chest compressions performed by the rescuer based at least in part on the values for the depths of the plurality of the chest compressions and the determination of whether the rescuer is releasing the chest of the patient.

Embodiments can include one or more of the following.

Determining whether the rescuer is releasing the chest of a patient during manual CPR chest compressions can include determining a frequency at which light is detected by the light sensor, comparing the determined frequency with a compression rate obtained from the accelerometer, and determining that the rescuer is not releasing the chest of a patient if the determined frequency at which light is detected by the light sensor is less than the compression rate obtained from the accelerometer.

Providing the feedback to the rescuer about chest compressions can include displaying on a graphical display screen of a defibrillator, an indication of the depths of one or more of the plurality of the chest compressions, the rate of the chest compressions, and a release indicator.

Providing the feedback to the rescuer about chest compressions can include displaying a release indicator where the amount of fill in the release indicator varies to indicate whether the rescuer is fully releasing between chest compressions.

Providing the feedback to a rescuer about chest compressions can include displaying an icon that indicates whether the chest compressions are being performed properly.

The method can also include receiving information about the patient's heart activity and displaying on a graphical display, with the feedback about chest compressions, an electrocardiogram of the patient.

The computing unit can be integrated with a portable defibrillator.

The computing unit can be a touchscreen tablet computer.

In some aspects, an external defibrillator includes a light sensor arranged to contact a patient and obtain measurements regarding light detection, a computing unit connected to memory that stores computer instructions for determining, based on the information from the light sensor, whether a rescuer is releasing the chest of a patient during manual CPR chest compressions, and a video display screen for displaying feedback to a rescuer about chest compressions performed by the rescuer based at least in part on the determination of whether the rescuer is releasing the chest of the patient.

Embodiments can include one or more of the following.

The computing unit can be configured to determine whether the rescuer is releasing the chest of a patient during manual CPR chest compressions by determining a frequency at which a threshold amount of light is detected by the light sensor, comparing the determined frequency with a compression rate obtained from an accelerometer, and determining that the rescuer is not releasing the chest of a patient if the determined frequency at which a threshold amount of light is detected by the light sensor is less than the compression rate obtained from the accelerometer.

The feedback to the rescuer about chest compressions can include a release indicator.

An amount of fill in the release indicator can vary to indicate whether the rescuer is fully releasing between chest compressions.

The feedback to the rescuer about chest compressions can include an icon that indicates whether the chest compressions are being performed properly.

The external defibrillator can also include one or more sensors configured to obtain information about the patient's heart activity.

The video display can be further configured to display an electrocardiogram of the patient with the feedback about chest compressions.

In some additional aspects, a method for providing adaptive Cardiopulmonary Resuscitation (CPR) treatment to a person in need of emergency assistance includes obtaining, by a computing unit, from an accelerometer positioned to move in coordination with a patient's breastbone values for depths of a plurality of the chest compressions, obtaining, by a computing unit, from a capacitive touch sensor affixed to the patient information about contact with the sensor, determining, based on the information from the capacitive touch sensor, whether a rescuer is releasing the chest of a patient during manual CPR chest compressions, and providing feedback to a rescuer about chest compressions performed by the rescuer based at least in part on the values for the depths of the plurality of the chest compressions and the determination of whether the rescuer is releasing the chest of the patient.

Embodiments can include one or more of the following.

Determining whether the rescuer is releasing the chest of a patient during manual CPR chest compressions can include determining a frequency at which contact with the capacitive touch sensor is detected based on the information from the capacitive touch sensor, comparing the determined frequency with a compression rate obtained from the accelerometer, and determining that the rescuer is not releasing the chest of a patient if the determined frequency at contact is detected by the capacitive touch sensor is less than the compression rate obtained from the accelerometer.

Providing the feedback to the rescuer about chest compressions can include displaying on a graphical display screen of a defibrillator, an indication of the depths of one or more of the plurality of the chest compressions, the rate of the chest compressions, and a release indicator.

Providing the feedback to the rescuer about chest compressions can include displaying a release indicator where the amount of fill in the release indicator varies to indicate whether the rescuer is fully releasing between chest compressions.

Providing the feedback to a rescuer about chest compressions can include displaying an icon that indicates whether the chest compressions are being performed properly.

The method can also include receiving information about the patient's heart activity and displaying on a graphical display, with the feedback about chest compressions, an electrocardiogram of the patient.

In some additional aspects, an external defibrillator includes a capacitive touch sensor arranged to contact a patient and obtain measurements regarding contact with the capacitive touch sensor, a computing unit connected to memory that stores computer instructions for determining, based on the information from the capacitive touch sensor, whether a rescuer is releasing the chest of a patient during manual CPR chest compressions, and a video display screen for displaying feedback to a rescuer about chest compressions performed by the rescuer based at least in part on the determination of whether the rescuer is releasing the chest of the patient.

Embodiments can include one or more of the following.

The computing unit can be configured to determine whether the rescuer is releasing the chest of a patient during manual CPR chest compressions by determining a frequency at which a capacitance indicative of contact of a rescuer's hands with the capacitive touch sensor is detected by the capacitive touch sensor, comparing the determined frequency with a compression rate obtained from an accelerometer, and determining that the rescuer is not releasing the chest of a patient if the determined frequency at which a threshold amount of light is detected by the light sensor is less than the compression rate obtained from the accelerometer.

The feedback to the rescuer about chest compressions can include a release indicator with an amount of fill in the release indicator varying to indicate whether the rescuer is fully releasing between chest compressions.

The feedback to the rescuer about chest compressions can include an icon that indicates whether the chest compressions are being performed properly.

The defibrillator can be further configured to receive information about the patient's heart activity and displaying on a graphical display, with the feedback about chest compressions, an electrocardiogram of the patient.

Other features and advantages will be apparent from the description and drawings, and from the claims.

DESCRIPTION OF DRAWINGS

FIGS. 6A and 6B are diagrams of a victim receiving CPR.

FIGS. 7A and 7B are diagrams showing the placement of the hands relative to a light sensor during the administration of CPR to a victim.

DETAILED DESCRIPTION

This description discusses systems and techniques for providing feedback to a user/rescuer about the quality of CPR chest compressions. In general, a defibrillation device includes a light sensor attached to a patient or a CPR sensor and configured to provide feedback to a rescuer about whether the rescuer is appropriately releasing the chest of the victim during chest compressions.

Figures 1A, 1B:
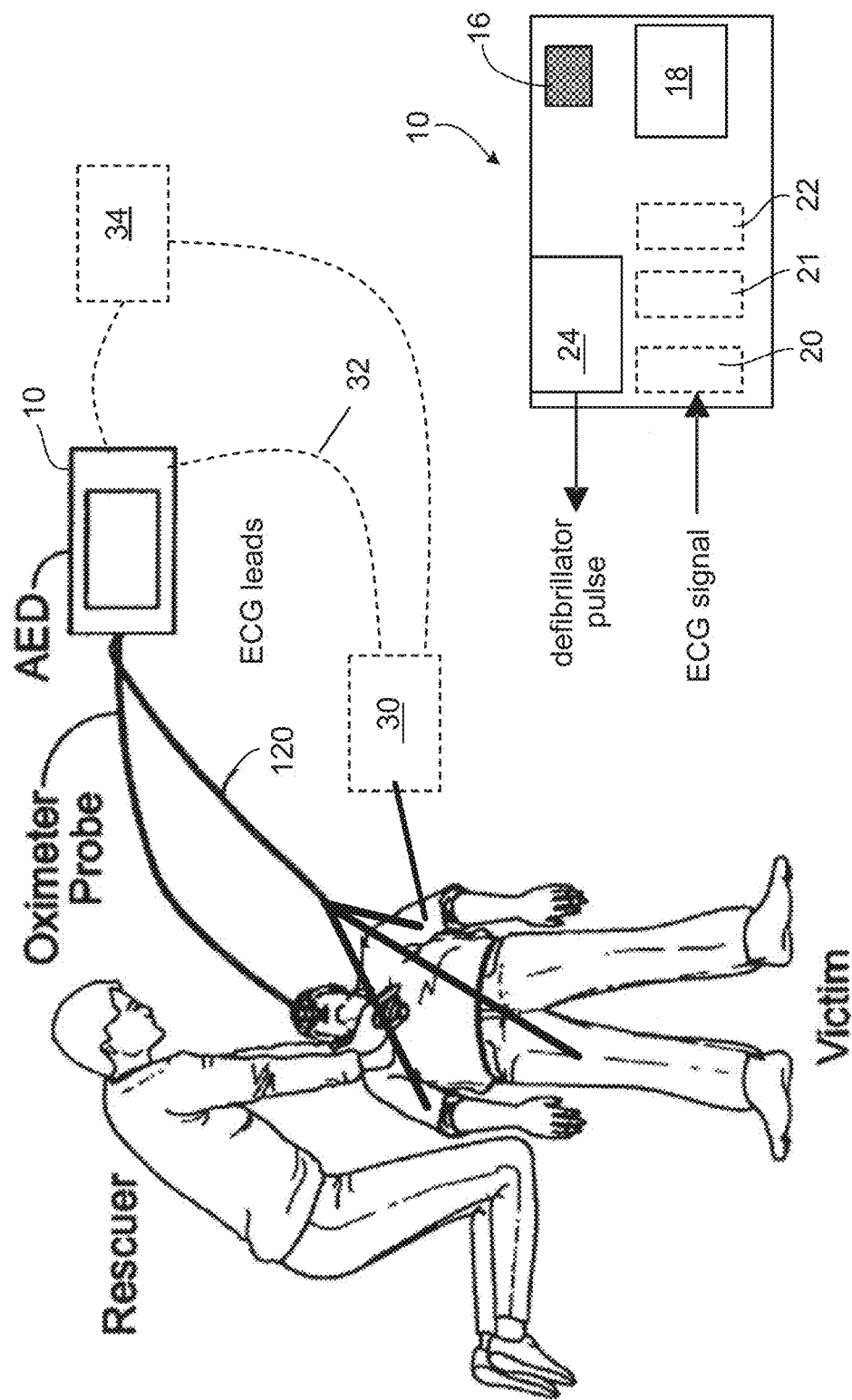
FIG. 1A is a diagram of one implementation including an automatic electronic defibrillator (AED) and a multiple lead electrocardiograph (ECG) device.
FIG. 1B is a diagram of the AED of FIG. 1A.

Referring now to FIG. 1A, an AED 10 is shown that may be used to provide a defibrillation shock at an appropriate time. In the figure, which shows an example implementation, a rescuer uses an AED 10 to automatically monitor a victim during cardiac resuscitation. The AED 10 uses measured ECG signals to monitor the victim's heart, and charges the defibrillation device within the AED while the victim is resuscitated using chest compressions techniques. In some examples, the manner in which the defibrillation device is charged (e.g., the rate of charge, the total amount of charge stored) can be based on the measured ECG signals. Advantageously, charging the defibrillation device during CPR chest compressions reduces the amount of time that the victim is not receiving chest compressions because, if a shockable rhythm exists, the device is armed and ready to deliver the shock as soon as the rescuer completes the chest compressions.

As shown in FIG. 1B, the AED 10 includes a speaker 16, a display screen 18, an analog-to-digital converter 20, a processor 22, and a defibrillator pulse generator 24. The analog-to-digital converter 20 is connected to a set of ECG leads that are in turn attached to the victim. The ECG leads pass signals to the processor 22 for monitoring the electrical rhythms of the victim's heart. The converter 20 sends the signals from the ECG leads to the processor 22. The processor 22 monitors the victim's heart for dangerous rhythms using the ECG signals while the victim is resuscitated using chest compressions techniques. If the AED 10 detects a dangerous heart rhythm, the AED 10 generates an alert signal.

The alert signal is noticeable to the rescuer. The AED 10 can generate a defibrillating shock to the victim when the rescuer issues a command to the AED 10 directing such a shock. The defibrillating shock is intended to remedy the dangerous rhythm of the victim's heart.

The AED 10 also includes a charging module that may be configured to charge the AED during chest compressions. The module can adaptively charge the AED based on monitored ECG signals and patient age. In some examples, the defibrillator is pre-charged only if a shockable rhythm is likely to exist as determined by analysis of the monitored ECG signals. In some additional examples, the level of charge for the device is determined and set based on the monitored ECG signals. In some additional examples, the method of charging (e.g., the rate of charge) varies based on the monitored ECG signals in an effort to conserve power. For example, if time allows, a capacitor may be charged more slowly than it normally would in order to conserve power, but still ensure that the capacitor will reach its full charge just as the defibrillator is needed by the rescuer.

The AED 10 uses a rhythm advisory method for, a) quantifying the frequency-domain features of the ECG signals; b) differentiating normal and abnormal ECG rhythms, such as VF; c) detecting the onset of abnormal ECG rhythms; and d) making decisions about the physiological states of the heart. This frequency-domain measure can be reliable with or without the presence of the chest compression artifact in the ECG signals. The AED 10, after identifying the current physiological state of the heart, can make a decision about appropriate therapeutic action for the rescuer to make and communicate the action to the rescuer using the speaker 16 and the display screen 18.

The AED 10 may incorporate functionality for performing additional therapeutic actions such as chest compressions, ventilations, or delivery of intravenous solution-containing metabolic or constitutive nutrients. Based on the results of the analysis of the rhythm advisory method, the AED 10 may automatically deliver the appropriate therapy to the patient.

The AED 10 may also be configured in "advisory" mode wherein the AED 10 will prompt the caregiver after the AED 10 has made a determination of the best therapy, and acknowledgement by the caregiver/device operator, in the form of a button press or voice-detected acknowledgement, is required before therapy is delivered to the patient.

The AED 10 analyzes the ECG signals to predict defibrillation success as well as to decide whether it is appropriate to defibrillate or to deliver an alternative therapy such as chest compressions, drugs such as epinephrine, constitutive nutrients such as glucose, or other electrical therapy such as pacing.

In some examples, one or more therapeutic delivery devices 30 automatically deliver the appropriate therapy to the patient. The therapeutic delivery devices 30 can be, for example, a portable chest compression device, a drug infusion device, a ventilator and/or a device that includes multiple therapies such as defibrillation, chest compression, ventilation and drug infusion. The therapeutic delivery devices 30 are physically separate from the defibrillator AED 10, and control of the therapeutic delivery devices 30 may be accomplished by a communications link 32. The communications link 32 may take the form of a cable but preferably the link 32 is via a wireless protocol.

In other examples, control and coordination for the overall resuscitation event and the delivery of the various therapies may be accomplished by a device 34 or processing element that is external to the AED 10. For instance, the device 34 may download and process the ECG data from the AED 10; analyze the ECG signals, perform relevant determinations like those discussed above and below based on the analysis, and control the other therapeutic devices 30, including the AED 10. In other examples, the AED 10 may perform all the processing of the ECG, including analyzing the ECG signals, and may transmit to the control device 34 only the final determination of the appropriate therapy, whereupon the control device 34 would perform the control actions on the other linked devices 30.

Chest compression artifacts can be separated from the ECG signal components, making it possible for the AED 10 to process the ECG signal without halting the processing during chest compressions. Exemplary methods for analyzing the ECG signal to determine if a shockable rhythm exists are described, for example, in U.S. Pat. No. 7,565,194, titled "ECG Rhythm Advisory Method," the contents of which are hereby incorporated by reference in their entirety.

It has been recognized that good chest compressions during CPR is essential to saving more victims of cardiac arrest. The compression rate recommended by the American Heart Association in its guidelines is equal or greater than 100 compressions per minute. Many studies have reported that the discontinuation of chest compressions, such as is commonly done for ECG analysis and charging of a defibrillator, can significantly reduce the recovery rate of spontaneous circulation and 24-hour survival rate. Because of safety issues with delivery of a high voltage defibrillation shocks with voltages of 1000-2000 volts, rescuers are taught to cease chest compressions and remove their hands from the victim's chest before initiating the defibrillation shock. By analyzing ECG signals during chest compressions as a mechanism to permit earlier charging of an energy delivery device (e.g., a capacitor) in a defibrillator device, the gaps in providing chest compressions can be reduced, and patient care increased.

Figure 2:
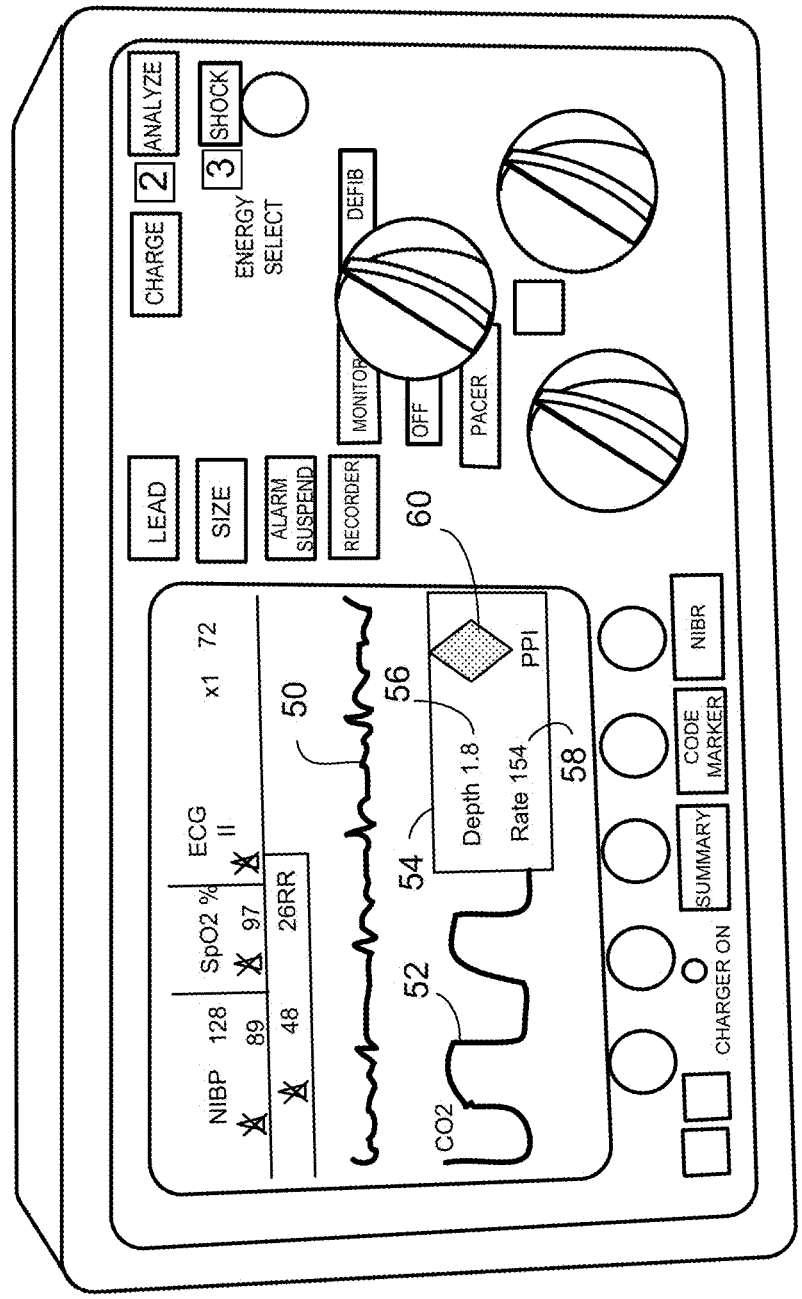
FIG. 2 is a diagram of a defibrillation device with a display.

FIG. 2 shows a defibrillation device 50 with a display portion 52 that provides information about patient status and CPR administration quality during the use of the defibrillator device. The data is collected and displayed in an efficient and effective manner to a rescuer. As shown on display 52, during the administration of chest compressions, the device 50 displays information about the chest compressions in box 54 on the same display as a filtered ECG waveform 51 and a $CO_2$ waveform 51 (alternatively a $SpO_2$ waveform can be displayed).

During chest compressions, the ECG waveform is generated by gathering ECG data point and accelerometer readings and filtering the motion induced (e.g., CPR induced) noise from the ECG waveform. Measurement of velocity or acceleration of chest compression during chest compressions can be performed according to the techniques taught by U.S. Pat. No. 7,220,335, Method and Apparatus for Enhancement of Chest Compressions During Chest Compressions, the contents of which are hereby incorporated by reference in their entirety. Displaying the filtered ECG waveform helps clinicians reduce interruptions in CPR because the displayed waveform is easier for the rescuer to decipher. If the ECG waveform is not filtered, artifacts from manual chest compressions make it difficult to discern the presence of an organized heart rhythm unless compressions are halted. Filtering out this artifact allows clinicians to view the underlying rhythm without stopping chest compressions.

As shown in display 50, the filtered ECG waveform 51 is a full length waveform filling the entire span of the display device while the second waveform (e.g., the $CO_2$ waveform 52) is a partial length waveform and fills only a portion of the display. A portion of the display beside the second waveform provides the CPR information in box 54. For example, the display splits the horizontal area for the second waveform in half, displaying waveform 52 on left and CPR information on the right in box 54.

The CPR information in box 54 is automatically displayed when compressions are detected. The information about the chest compressions displayed in box 54 includes rate 58 (e.g., number of compressions per minute) and depth 56 (e.g., depth of compressions in inches or millimeters). The rate and depth of compressions can be determined by analyzing accelerometer readings. Displaying the actual rate and depth data (in addition to or instead of an indication of whether the values are within or outside of an acceptable range) is believed to provide useful feedback to the rescuer. For example, if an acceptable range for chest compression depth is between 1.5-2 inches, providing the rescuer with an indication that his/her compressions are only 0.5 inches can allow the rescuer to determine how to correctly modify his/her administration of the chest compressions.

The information about the chest compressions displayed in box 514 also includes a perfusion performance indicator (PPI) 60. The PPI 60 is a shape (e.g., a diamond) with the amount of fill in the shape differing to provide feedback about both the rate and depth of the compressions. When CPR is being performed adequately, for example, at a rate of about 100 compressions/minute (CPM), with the depth of each compression greater than 1.5 inches, the entire indicator will be filled. As the rate and/or depth decreases below acceptable limits, the amount of fill lessens. The PPI 60 provides a visual indication of the quality of the CPR such that the rescuer can aim to keep the PPI 60 completely filled. While some exemplary types of information displayed to the rescuer have been described herein, additional information about CPR quality and physiological parameters of the victim can be displayed in conjunction with or instead of the information described herein. For example, a release indication can be displayed with other information about the CPR quality of measured physiological parameters. Exemplary displays and measurements are described, for example, in Ser. No. 13/025,348 filed on Feb. 11, 2011, now U.S. Pat. No. 8,880,166, issued on Nov. 4, 2014 and entitled "DEFIBRILLATOR DISPLAY" and in Ser. No. 13/081,217 field on Apr. 6, 2011, now U.S. Pat. No. 9,364,625, issued on Jun. 14, 2016 and entitled "WIRELESS VENTILATOR REPORTING," the contents of each of which are hereby incorporated by reference.

In addition to measuring information about the rate and depth of CPR chest compressions, in some examples the defibrillator device provides information about whether the rescuer is fully releasing his/her hands at the end of a chest compression. For example, as a rescuer tires, the rescuer may begin leaning on the victim between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial.

Figure 3:
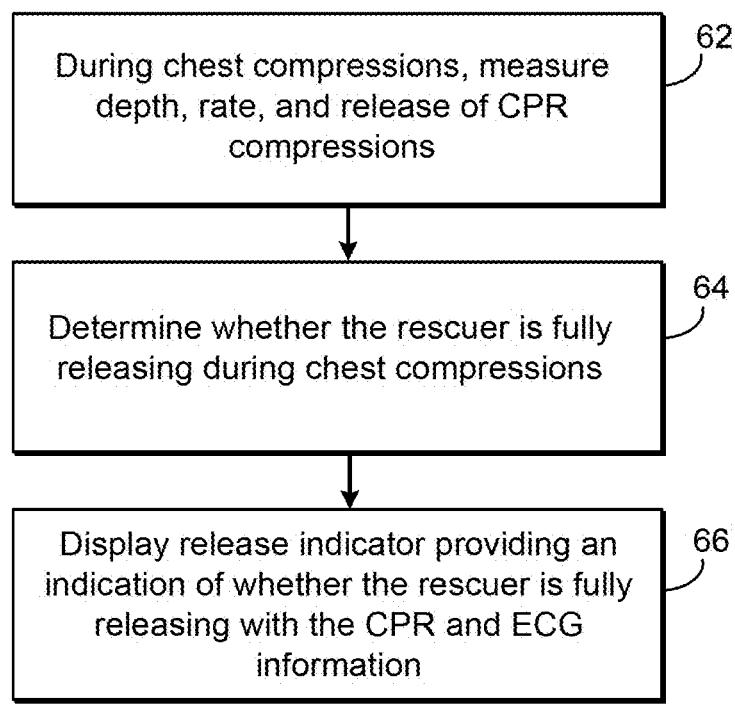
FIG. 3 is a flow chart showing actions taken to provide a release indicator.
Figure 4A:
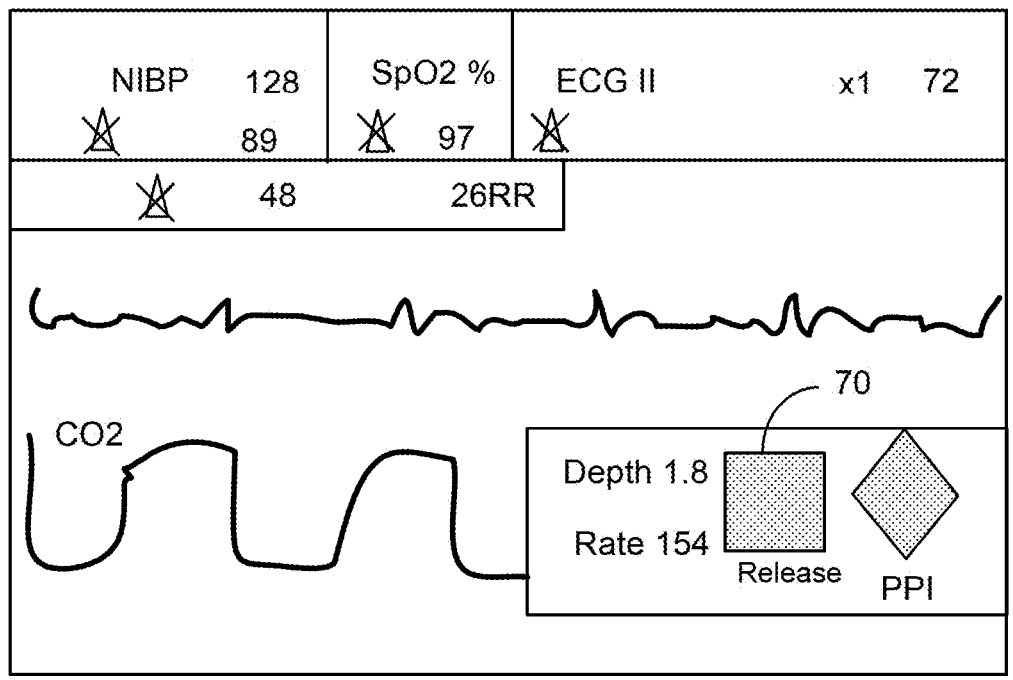
FIGS. 4A and 4B are screenshots showing exemplary information presented on a defibrillator display.
Figure 4B:
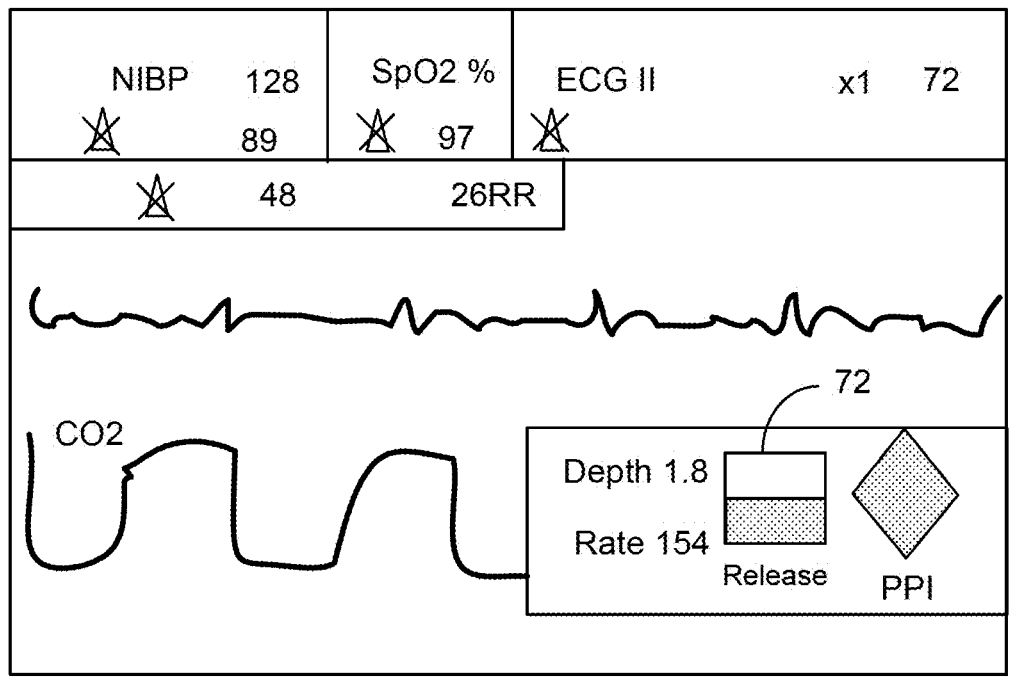

FIG. 3 is a flow chart showing actions taken to provide an indication of whether a rescuer is fully releasing between chest compressions. At box 62, the defibrillator device measures depth, rate, and release of CPR chest compressions. The depth, rate, and release of CPR chest compressions can be determined based on information collected from an accelerometer, light sensor, capacitive touch sensor, or other devices. Based on the collected information, at box 64, the defibrillator determines whether the rescuer is fully releasing between chest compressions. At box 66, the defibrillator provides an indicator on a display that includes information about whether the rescuer is fully releasing. For example, the display on the defibrillator can include a release indication box where the amount of fill in the box varies to indicate whether the rescuer is fully releasing between chest compressions. For example, as shown in FIG. 4A, when the rescuer is fully releasing the box 70 can be fully filled. When the rescuer is not fully releasing the amount of fill in the release indication box is decreased such that the box is only partially filled (e.g., as shown in box 72 of FIG. 4B).

Figure 5:
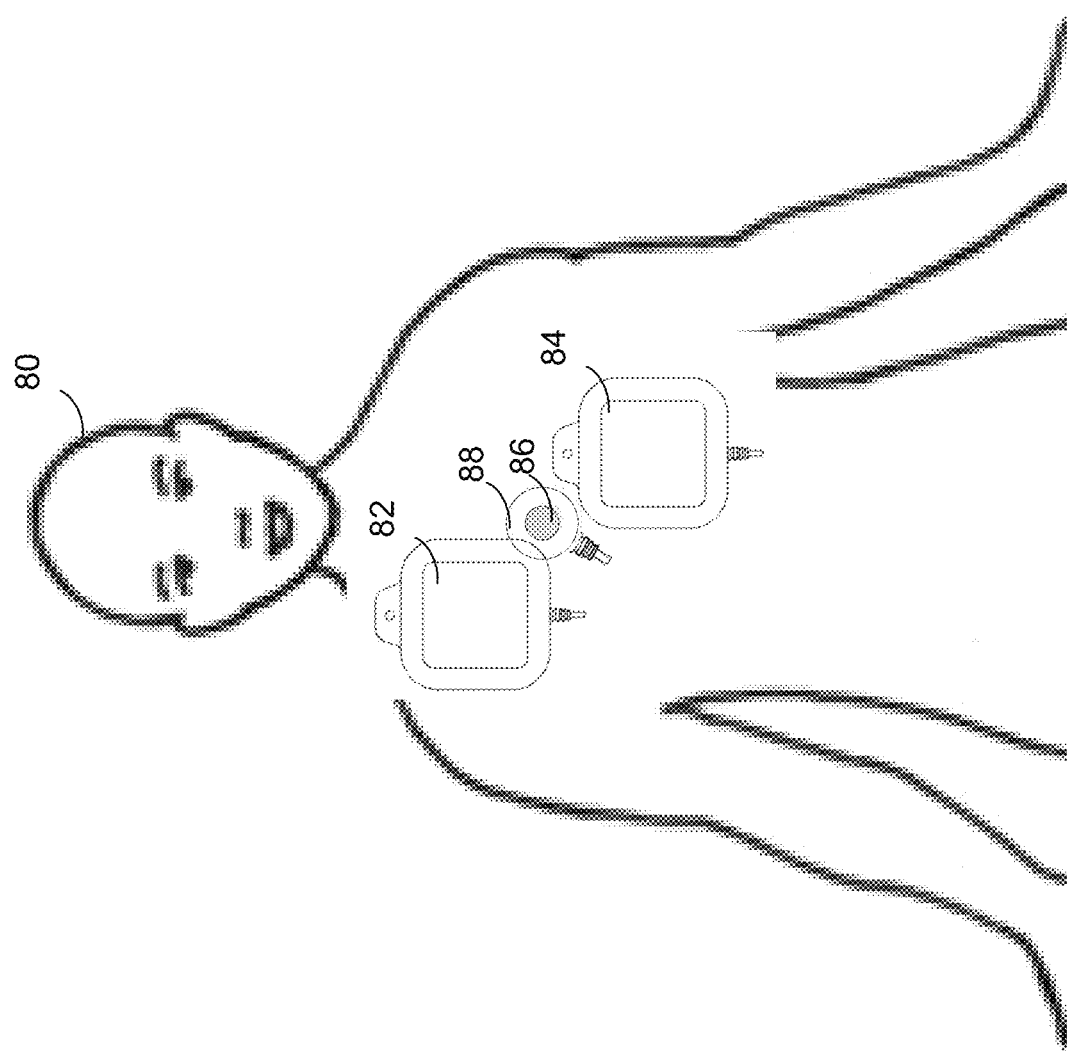
FIG. 5 is a diagram of defibrillation electrodes attached to a victim.

In some examples, the depth and rate of CPR chest compressions can be determined based on information collected from an accelerometer while the release of the CPR chest compressions can be based on information collected from a light or capacitive touch sensor. For example, as shown in FIG. 5, a CPR monitoring device 86 that includes a light sensor or capacitive touch sensor 88 and an accelerometer can be affixed to a victim's chest at a location corresponding to the location of the rescuer's hands when delivering manual chest compressions prior to the administration of CPR. The light sensor measures light impinging on the sensor and provides the information to a computing device in the defibrillator. The defibrillator processes the information to determine whether the rescuer's hands are in contact with the light sensor 88. More particularly, because the device 86 is affixed to the victim's chest or on top of the CPR sensor at a location corresponding to the location of the rescuer's hands when delivering manual chest compressions, the presence or absence of light detection by the light sensor 88 can be used to determine whether the rescuer is fully releasing the chest of the victim during the administration of chest compressions.

The light sensor 88 can be any device that is used to detect light. Exemplary light sensors include photocells or photoresistors that change resistance when light shines on it, charged coupled devices (CCD) that transport electrically charged signals, photomultipliers that detect light and multiply it, and the like. Capacitive sensing is a technology based on capacitive coupling between conductive or has a dielectric different than that of air and the sensor. When the human hands approaches or touches the capacitive sensor, this detects this movement or touch of the hand and measure a change in capacitance. The level of capacitance can be used by the processor or device to determine whether the rescuer hand is touching the capacitor sensor pad.

FIGS. 6A-B and 7A-B show exemplary light sensor during CPR compressions. As shown in FIGS. 6A and 7A, when the rescuer's hands 92 are raised away from the victim's chest and are not in contact with the victim's chest 90 (e.g., when the rescuer releases from a compression), the light sensor 88 is uncovered. Thus, when the rescuer's hands are raised away from the victim's chest light 96 can reach the light sensor 88 and the light sensor detects the presence of the light 96. In contrast, as shown in FIGS. 6B and 7B, when the rescuer's hands 92 are in contact with the victim's chest 90 (e.g., when the rescuer is providing a compression) the light sensor 88 is covered. When the light sensor is covered, light is not able to reach the light sensor 88. Thus, the presence and absence of light measured by the light sensor can be used to determine whether the rescuer is fully releasing his/her hands from the victim's chest 90; when light is detected the rescuer has released and when light is not detected the rescuer is maintaining physical contact with the victim.

In some examples, the information from the light sensor can be compared to CPR compression rate information from the accelerometer to determine whether the user is releasing the victim's chest fully. More particularly, if the rescuer is releasing the victim's chest fully, light should be observed by the light sensor for every compression. Thus, the defibrillation device can determine a frequency at which a threshold amount of light is detected by the light sensor and compare the determined frequency with a compression rate obtained from the accelerometer. If the determined frequency from the light sensor is the same (or within an acceptable range from) the compression rate obtained from the accelerometer, the defibrillation device can determine that the rescuer is appropriately releasing the victim's chest. On the other hand, if the frequency from the light sensor is less than the compression rate, the defibrillation device can determine that the rescuer is not appropriately releasing the victim's chest.

While in the example described above, the presence/absence of light was used to determine the release of the rescuer's hands from the victim's chest, in some additional examples a change in light measured by the light sensor 88 can be used to determine the presence/absence of the rescuer's hands. For example, the rescuer may not fully cover the light sensor 88 when providing compressions. However, if a portion of the light sensor 88 is covered, a change in the intensity or amount of light measured by the light sensor will be observed when the rescuer lifts his/her hands. This change in intensity can be used to determine presence/absence of the rescuer's hands.

In some additional examples, the light sensor 88 can be used to detect the removal of the electrodes from a package and can be used to begin instructions to a rescuer about how to apply the electrodes to the victim.

Figure 8A:
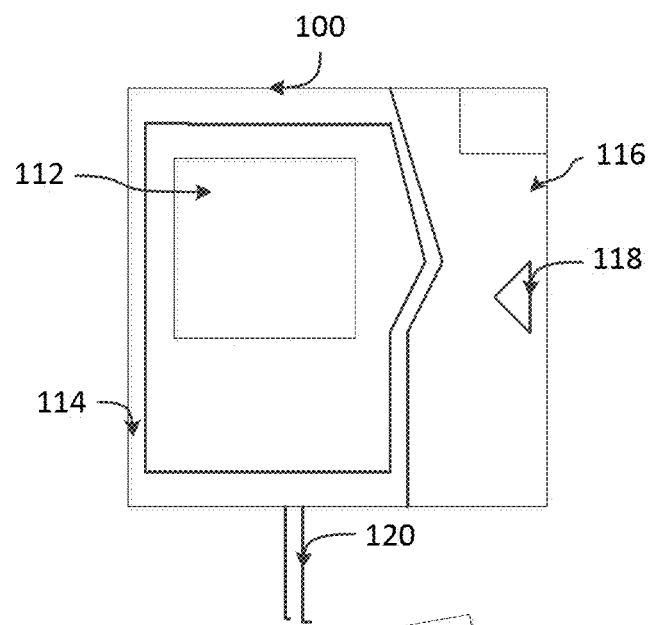
FIG. 8A shows an electrode package.

FIG. 8A shows an assembled electrode package 110 with multiconductor electrical lead 120 and label 112. The package is opened by grasping the loose flaps 116 at arrow label 118, and peeling back the top flap. As the flaps are pulled apart, releaseable peripheral adhesive 114 parts. When a light sensor is included in the assembled electrode package 110, light is unable to impinge on the light sensor 161. As such, information from the sensor can be used to determine that the rescuer has not yet opened the electrode package regardless of whether the leads 120 have been plugged into a defibrillation device. As such, if the defibrillation device detects that the leads 120 have been inserted into the defibrillation device but the light sensor 161 does not indicate the presence of light, the defibrillation device can provide instructions to the rescuer about how to open the electrode package 110.

Figure 8B:
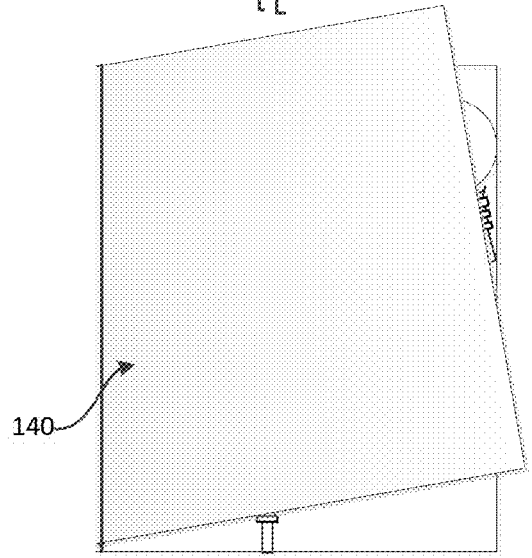
FIGS. 8B and 8C show defibrillation electrodes prior to removal from a backing.
Figure 8C:
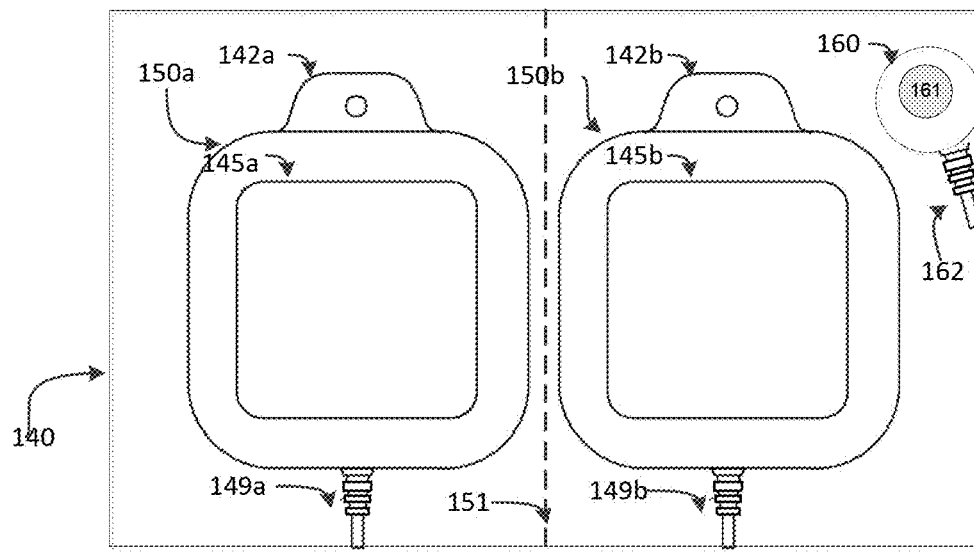

FIGS. 8B and 8C show views of the electrodes 150a and 150b, an accelerometer 160, a light sensor 161, and styrene sheet 140 after removal from the electrode package 110. Before the package is opened, the styrene sheet 140 is folded along fold line 151 in the form of a closed book (e.g., as shown in FIG. 8B), with the electrodes 50a and 50b and accelerometer 60 peelably attached to the interior facing surfaces of the book. The accelerometer works with electronics in the defibrillator to determine the depth of compressions during CPR. The light sensor 161 works with electronics in the defibrillator to determine whether the rescuer is appropriately releasing the victim's chest between compressions (e.g., as described herein). ECG electrodes (not shown) are built into one of electrode 150a or 150b (each is located at approximately the corners of the triangular shape of the electrode). Until the book is unfolded, the light sensor 161 is covered by the opposite side of the styrene sheet 140 and light is unable to impinge on the light sensor. On opening the package, the book is unfolded, so that the electrodes and accelerometer are presented to the user as shown in FIG. 8C. Upon unfolding the book, the light sensor 161 is uncovered and light is able to reach the light sensor. Thus, the unfolding of the book (and the resulting light measurement from the sensor 161) indicates to the defibrillation device that the user has opened the package 110 and is ready to receive information (e.g., audio or visual instructions) about the application of the electrodes to the victim.

Figure 9A:
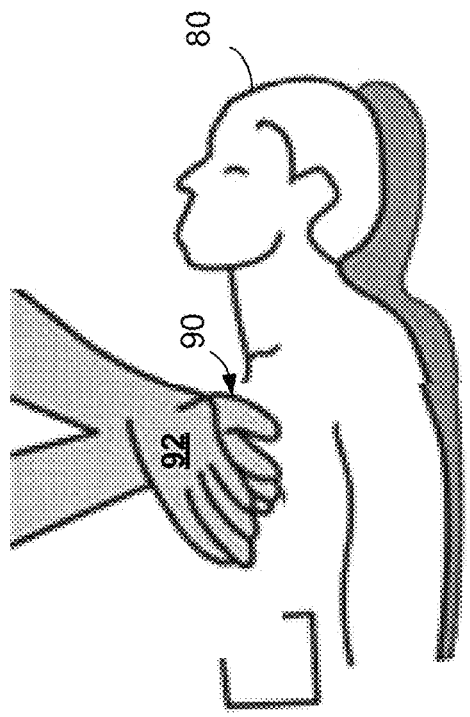
FIGS. 9A and 9B are diagrams of a victim receiving CPR.
Figure 9B:
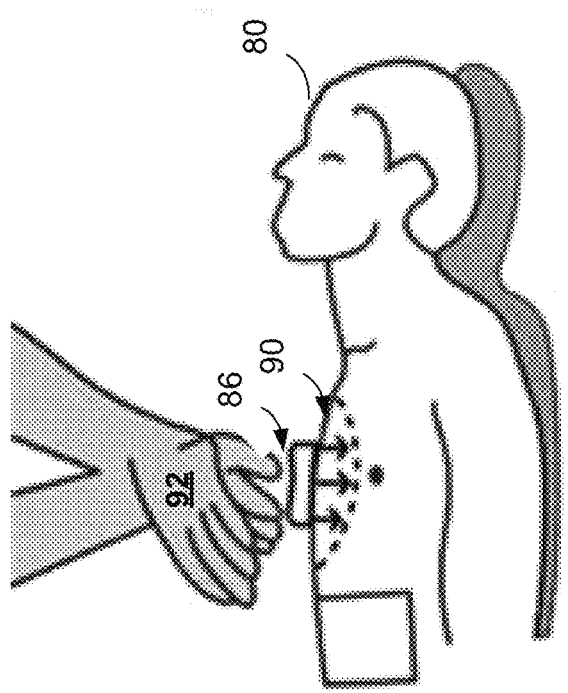
Figure 10A:
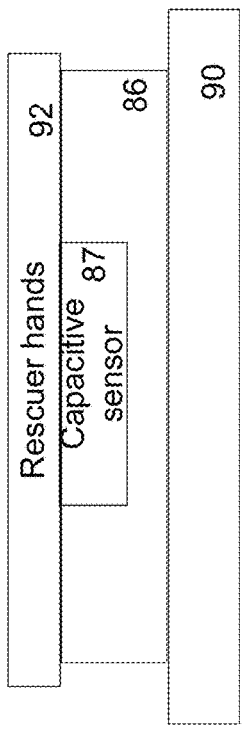
FIGS. 10A and 10B are diagrams showing the placement of the hands relative to a capacitance sensor during the administration of CPR to a victim.
Figure 10B:
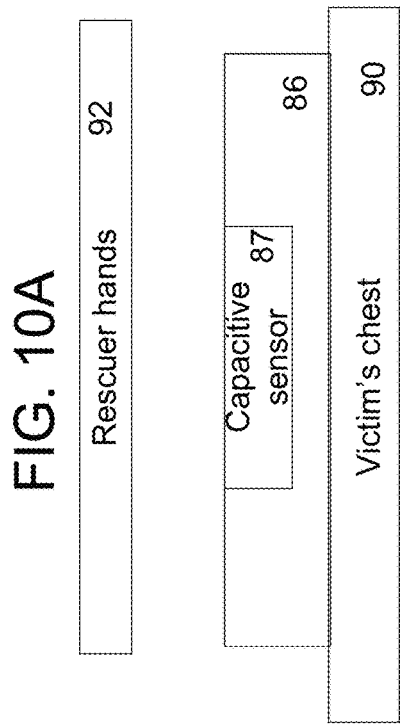

FIGS. 9A-B and 10A-B show capacitance sensor during CPR compressions. As shown in FIGS. 9A and 10A, when the rescuer's hands 92 are raised away from the victim's chest and are not in contact with the victim's chest 90 (e.g., when the rescuer releases from a compression), the capacitance sensor 87 is uncovered. Thus, when the rescuer's hands are raised away from the victim's chest capacitance measured by the capacitance sensor 87 is based on the dielectric of air. In contrast, as shown in FIGS. 9B and 10B, when the rescuer's hands 92 are in contact with the victim's chest 90 (e.g., when the rescuer is providing a compression) the capacitance sensor 87 is covered and contact is made between the rescuer's hands and the sensor 87. When the human hands approach or touch the capacitive sensor 87, the sensor 87 detects this movement or touch of the hand and measures a change in capacitance. Thus, the measured capacitance level can be used by the processor or device to determine whether the rescuer hand is touching the capacitor sensor 87 and can be used to determine whether the rescuer is fully releasing his/her hands from the victim's chest 90; when capacitance remains at a level indicating that the rescuer's hands are in contact with the capacitance sensor 87, the rescuer is not fully releasing his/her hands between compressions.

In some examples, the information from the capacitance sensor can be compared to CPR compression rate information from the accelerometer to determine whether the user is releasing the victim's chest fully. More particularly, if the rescuer is releasing the victim's chest fully, a change in capacitance should be observed by the capacitance sensor for every compression. Thus, the defibrillation device can determine a frequency at which a threshold change in capacitance is detected by the capacitance sensor and compare the determined frequency with a compression rate obtained from the accelerometer. If the determined frequency from the capacitance sensor is the same (or within an acceptable range from) the compression rate obtained from the accelerometer, the defibrillation device can determine that the rescuer is appropriately releasing the victim's chest. On the other hand, if the frequency from the capacitance sensor is less than the compression rate, the defibrillation device can determine that the rescuer is not appropriately releasing the victim's chest.

While at least some of the embodiments described above describe techniques and displays used in conjunction with an AED device, similar techniques and displays can be used with other defibrillator devices. Exemplary professional grade defibrillator devices include the R series, E series, Propaq MD, or M series devices manufactured by ZOLL Medical, MA and the Philips MRX or Philips XL devices.

Additionally, the defibrillator may take the form of a wearable defibrillator such as the LifeVest, manufactured by ZOLL Medical (Chelmsford, Mass.).

Many other implementations other than those described may be employed, and may be encompassed by the following claims.

What is claimed is:

1. A system for assisting a rescuer in performing resuscitation activities on a patient, comprising:
    a chest compression sensor configured to sense movement of the patient's chest;
    a second sensor configured to sense information indicative of whether the rescuer's hand is in contact with or is not in contact with the patient's chest, wherein the second sensor is configured to be positioned on the patient's chest at a location corresponding to a location of the rescuer's hand when delivering chest compressions to the patient's chest;
    a feedback device configured to provide chest compression and chest release feedback; and
    a computing unit configured to:
        receive and process information from the chest compression sensor and the second sensor,
        determine chest compression rate and chest compression depth based upon movement information received from the chest compression sensor,
        determine whether the rescuer is releasing the patient's chest in between chest compressions based upon the information received from the second sensor,
        cause the feedback device to provide chest compression feedback based on the determined chest compression rate and chest compression depth, and
        cause the feedback device to provide chest release feedback based on the determination of whether the rescuer is releasing the chest in between chest compressions.

2. The system according to claim 1, wherein the feedback device comprises one or more of a visual display and an audio device.

3. The system of claim 2, wherein the chest compression feedback comprises a visual indication of at least one of the determined chest compression rate and the determined chest compression depth.

4. The system of claim 3, wherein the visual indication of the determined chest compression rate comprises a numerical value representing the chest compression rate.

5. The system of claim 3, wherein the visual indication of the determined chest compression depth comprises a numerical value representing the chest compression depth.

6. The system of claim 1, wherein the information received from the second sensor comprises the information indicative of whether the rescuer's hand is in contact with or is not in contact with the patient's chest.

7. The system of claim 1, wherein the computing unit is configured to identify occurrence of a chest compression based on the information received from the second sensor of whether the rescuer's hand is in contact with or is not in contact with the patient's chest.

8. The system of claim 7, wherein the computing unit is configured to calculate chest compression depth based on the information sensed by the chest compression sensor during the identified occurrence of the chest compression.

9. The system of claim 1, wherein the chest compression sensor comprises an accelerometer.

10. The system of claim 1, wherein the second sensor comprises a proximity sensor.

11. The system of claim 10, wherein the proximity sensor comprises a light sensor configured to obtain measurements regarding light detection.

12. The system of claim 10, wherein the proximity sensor comprises a capacitive touch sensor configured to obtain measurements regarding contact with the capacitance touch sensor.

13. The system of claim 1, further comprising a defibrillation pulse generator configured to generate a defibrillating shock to the patient.

14. The system of claim 1, wherein the computing unit is configured to determine whether the rescuer is releasing the patient's chest between chest compressions based, at least in part, on a sensed level of intensity from the second sensor.

15. The system of claim 14, wherein the computing unit is configured to compare a frequency of release based on a sensed level of intensity of the second sensor and the determined chest compression rate.

16. The system of claim 1, wherein the chest release feedback comprises a visual indication of whether the rescuer is releasing the chest in between chest compressions.

17. The system of claim 16, wherein the visual indication comprises a shape which is filled by a fill amount when the rescuer's hand fully releases the patient's chest between chest compressions, and wherein the fill amount is reduced when the rescuer's hand does not fully release the patient's chest between chest compressions.

18. The system of claim 1, wherein the chest compression feedback comprises a visual indication of an overall quality of chest compressions.

19. The system of claim 18, wherein the overall quality of chest compressions is derived from at least one of the determined chest compression rate, the determined chest compression depth, and the determination of whether the rescuer is releasing the chest in between chest compressions.

20. The system of claim 18, wherein the visual indication comprises a shape which is filled by a fill amount with the fill amount in the shape differing to provide feedback about both the chest compression rate and chest compression depth.

\* \* \* \* \*